(12) United States Patent
Ferster et al.

(10) Patent No.: US 6,273,026 B1
(45) Date of Patent: Aug. 14, 2001

(54) AUTOMATED SYSTEM AND METHOD FOR MEASURING AND EVALUATING AN ANIMAL'S RESPONSE DURING A BEHAVIORAL TEST

(75) Inventors: David Ferster, Evanston; Eva Redei, Chicago, both of IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/338,187

(22) Filed: Jun. 22, 1999

(51) Int. Cl.[7] .................................................. A01K 29/00
(52) U.S. Cl. ............................................................. 119/421
(58) Field of Search ........................ 119/421; 73/290 R, 73/290 V, 304 R, 304 C; 600/561, 393

(56) References Cited

U.S. PATENT DOCUMENTS

| | | | |
|---|---|---|---|
| 4,626,992 | * 12/1986 | Greaves et al. | 119/268 X |
| 4,723,511 | * 2/1988 | Solman et al. | 119/224 |
| 5,140,855 | * 8/1992 | Gruber | 119/215 X |
| 5,307,052 | * 4/1994 | Harrison et al. | 119/215 X |

* cited by examiner

*Primary Examiner*—Robert P. Swiatek
(74) *Attorney, Agent, or Firm*—McAndrews, Held & Malloy, Ltd.

(57) ABSTRACT

A method and system for automatically measuring an animal's response to his environment in a behavioral test that is indicative of the animal's mental or emotion state. For the behavioral test known as the Porsolt Forced Swim test, a pair of spaced electrodes is positioned in a tank of water in which an animal is placed. A current is applied to the electrodes to generate a voltage across the electrodes that varies with the height of the water at the electrodes and to thus provide an indication of the animal's movement in the water. The electrode signal is processed to determine the energy of the perturbations in the water caused by the animal's movement. This data is used to provide a graphical representation of the animal's activity over time. The data is also compared to one or more thresholds to distinguish various types of behavior, such as floating, swimming and climbing.

26 Claims, 4 Drawing Sheets

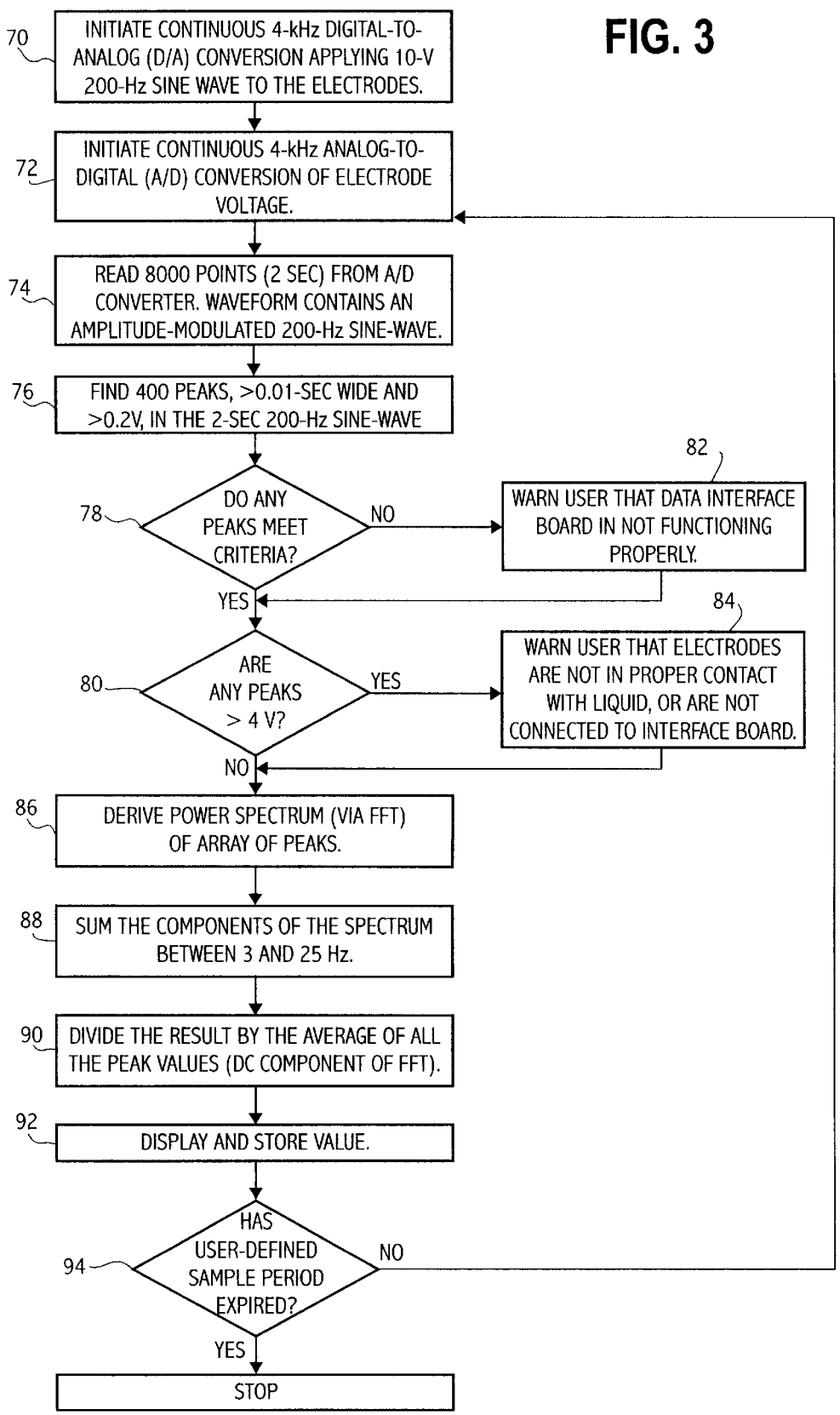

AUTOMATED SYSTEM AND METHOD FOR MEASURING AND EVALUATING AN ANIMAL'S RESPONSE DURING A BEHAVIORAL TEST

CROSS-REFERENCE TO RELATED APPLICATIONS N/A

STATEMENT REGARDING FEDERALLY SPONSORED RESEARCH OR DEVELOPMENT N/A

1. TECHNICAL FIELD

The present invention is directed to a system and method for automatically measuring an animal's response to its environment in a behavioral test to provide an indication of the animal's mental or emotional state.

2. BACKGROUND OF THE INVENTION

The Porsolt Forced Swim test is an accepted behavioral test performed to assess depression-like behavior in small animals such as rodents. This test is used for initial screening of new drugs for treating human affective disorders such as depression, stress, anxiety, psychosis, etc. This test is also used for screening genes involved in the etiology of human affective disorders.

In order to perform a Porsolt Forced Swim test, an animal is placed in a tank of water which has been filled to a level that is deep enough so that the animal is not able to support itself on the bottom of the tank, but that is sufficiently far from the top edge of the tank so that the animal cannot climb out. Most animals will swim or attempt to climb actively for some time after being placed in the tank. But gradually, the activity of the animal will lessen, presumably as the animal realizes that it cannot escape. As this happens, the animal will gradually spend more and more time simply floating on the surface of the water. The time, or the fraction of a fixed period of time, during which the animal actively swims and the time during which the animal floats is measured by human observation and used as an indication of the affect of the animal. Less time swimming and more time floating denotes "behavioral despair," an animal model of depression.

In order to score a Porsolt Forced Swim Test, the swimming of the animal is typically videotaped and the amount of floating and swimming is timed with a stop-watch or hand held counter. Although the Porsolt Test itself is very simple, the procedure for scoring the test is laborious and inherently subjective since criteria for floating or for active swimming or climbing may vary from one observer to another or even from time to time for a single observer.

BRIEF SUMMARY OF THE INVENTION

In accordance with the present invention, the disadvantages of prior systems for measuring, evaluating and/or scoring behavioral animal tests used to study or treat human affective disorders have been overcome. The system and method of the present invention automatically measure an animal's response to his environment in a behavioral test to provide an indication of the animal's mental or emotional state. The system and method provides an objective measurement of the animal's behavior quickly, reliably and reproducibly. It is capable of detecting subtle differences in behavior with much greater resolution than is possible with human observation.

More particularly, in accordance with the present invention, a pair of spaced electrodes are positioned in a tank of water in which an animal is placed for at least partial immersion of the electrodes. A current is applied to the electrodes and the voltage across the electrodes is measured to provide a waveform, the amplitude of which varies with the height of the water in the tank to provide an indication of the animal's behavior. The signal from the electrodes is then processed to provide data representing the behavior of the animal as indicative of the animal's mental or emotional state.

In accordance with one embodiment of the present invention, the electrode signal is processed to determine the energy of the perturbations in the water caused by the animal's movement. This data is used to provide a graphical representation of the animal's activity over time. The data is also compared to one or more thresholds to distinguish various types of behavior. For example, one threshold distinguishes between electrode signals that are indicative of the animal swimming and that are indicative of the animal floating. With this data, a graphical representation can be generated to illustrate the relative amounts of time that the animal was swimming and floating during a given test.

In accordance with another feature of the present invention, the electrode signal is filtered to remove low frequency components of the signal associated with movement of the water in the absence of animal movement. This filter allows the system to distinguish between water perturbations at the resonant frequency of the tank that will continue long after movement of the animal has stopped. Further, in order to compensate for the variability of the conductivity of the water used in the tank, the data is normalized with respect to the conductivity of the water when at rest.

These and other advantages and novel features of the present invention, as well as details of an illustrated embodiment thereof, will be more fully understood from the following description and drawings.

BRIEF DESCRIPTION OF THE DRAWING

FIG. 3 is a flow chart illustrating the software for processing the signal derived from the electrode assembly of FIG. 1 so as to provide data representing the behavior of the animal as indicative of the animal's mental or emotional state;

DETAILED DESCRIPTION OF THE INVENTION

Figure 1:
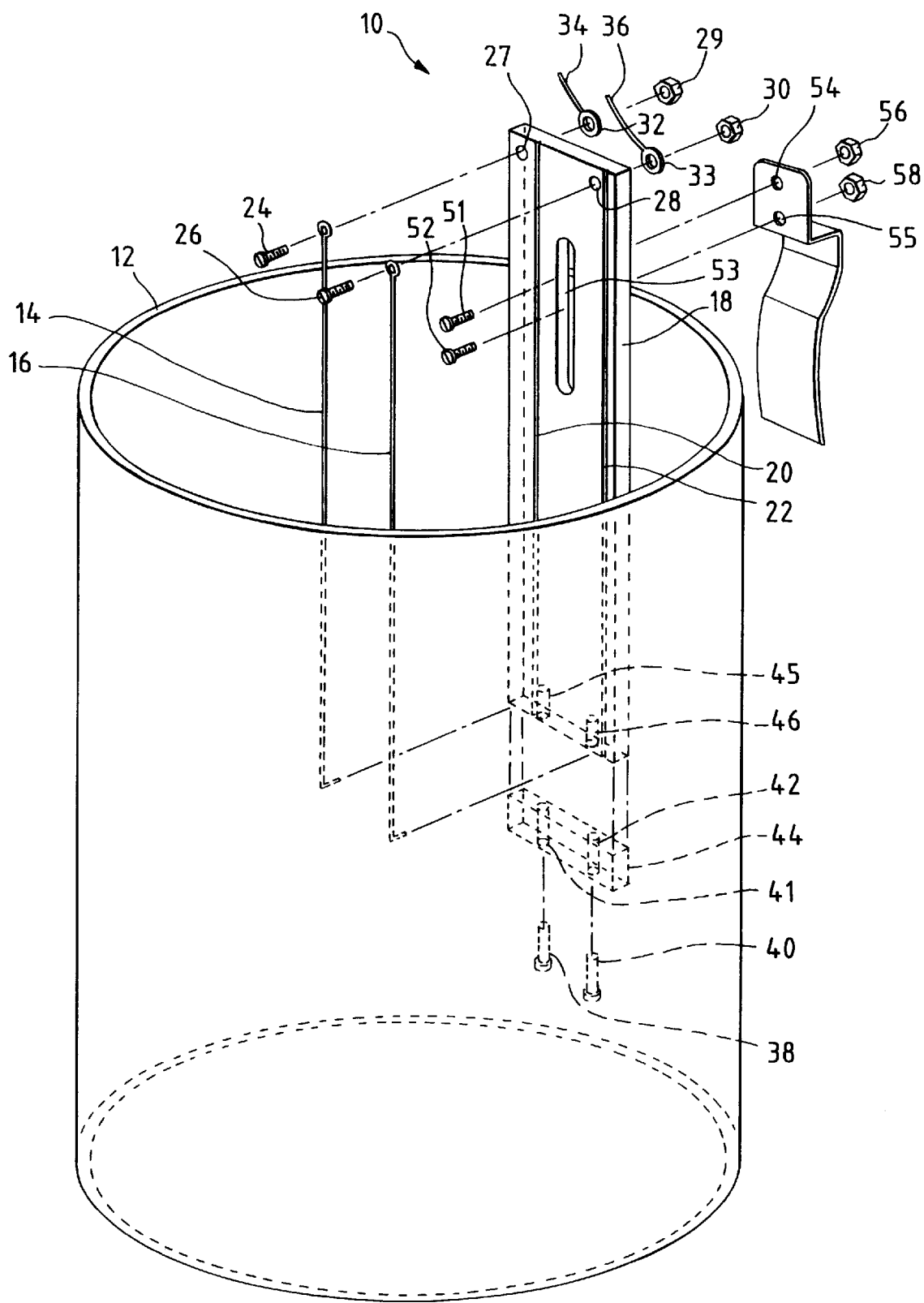
FIG. 1 is a perspective view of the water tank and an exploded view of the electrode or sensor assembly of the present invention.

In the illustrated embodiment of the present invention, an electrode assembly 10 as shown is FIG. 1 is positioned in a tank 12 of water in which an animal is placed in order to measure, evaluate and/or score a behavioral test such as the Porsolt Forced Swim test to provide an indication of the animal's mental or emotional state. The electrode assembly 10 includes a pair of spaced wire electrodes 14 and 16 immersed at least partially in the water of the tank 12. A small current is coupled to the electrodes to generate a voltage across the electrode wires 14 and 16 that is measured and processed as described in detail below. The voltage varies with the conductance/resistance of the water between the two electrode wires 14 and 16. This conductance is directly related to the height of the water above the tips of the electrode wires. The higher the water level, the broader the path for the current so that the measured voltage provides an indication of the height of the water in the tank.

As the animal swims, it typically disturbs the surface of the water, creating perturbations or waves therein. When the waves reach the electrode wires 14 and 16, the fluctuation in the water height at the electrodes results in fluctuations in the conductance between the two electrode wires 14 and 16. The voltage across the electrode wires therefor varies with the vigor with which the animal is moving so as to indicate whether the animal is floating, swimming or climbing.

The electrode wires 14 and 16 are preferably made of a corrosion resistant material such as platinum, silver-coated steel, stainless steel, etc. The electrodes should be sufficiently thin so that an animal cannot climb on them. For example, the electrodes are preferably less than 0.050 inches in diameter. The electrode wires 14 and 16 are held vertically and in parallel by a mounting plate 18. The wires 14 and 16 may be separated by a horizontal distance of, for example, 1–2 inches.

The mounting plate 18 is preferably made of plastic having a generally smooth outer surface with rounded edges to prevent climbing. The electrode wires 14 and 16 are placed in respective parallel and vertically extending V-shaped slots 20 and 22 formed in the mounting plate 18. At the mounting plate's upper surface, the electrode wires 14 and 16 are held in place by respective screws 24, 26 that extend through apertures 27, 28. The screws 24 and 26 are held in place by respective threaded nuts 29 and 30. A steel washer 32, 33 is disposed on the respective screw 24, 26 between the mounting plate 18 and the threaded nuts 29, 30 so as to provide an electrical connection between the wires 14 and 16 and a pair of wires 34 and 36 that are soldered to the washers 32 and 33. The wires 34 and 36 are then coupled to a computer for processing of the measured voltage as described below. The tips of the electrode wires 14 and 16 that are immersed in the water are held in place at the bottom of the mounting plate 18 by an end cap 44. Screws 38 and 40 extend through respective apertures 41 and 42 in the end cap 44 and into threaded apertures 45, 46 in the bottom of the mounting plate 18. When the end cap 44 is screwed onto the mounting plate 18, the end cap clamps the electrode tips securely in place. A spring clip 50 is attached to the back of the mounting plate 18 by a pair of screws 51, 52 that extend through an aperture 53 formed in the plate 18 and into respective apertures 54, 55 of the clip 50. The screws 51 and 52 are held in place by respective threaded nuts 56 and 58.

The electrode assembly is clipped onto a wall of the tank so that the spring clip 50 is on the outside of the tank and the electrode assembly is on the inside of the tank with the tips of the electrodes 14 and 16 protruding approximately 1.5 inches beneath the surface of the water in the tank. It should be appreciated, that the exact horizontal distance between the electrode wires 14 and 16 and the length of the electrodes that is submerged in the water will affect the size of the voltage picked up by the electrodes and the sensitivity of the sensor to ripples or perturbations of different wavelengths.

Figure 2:
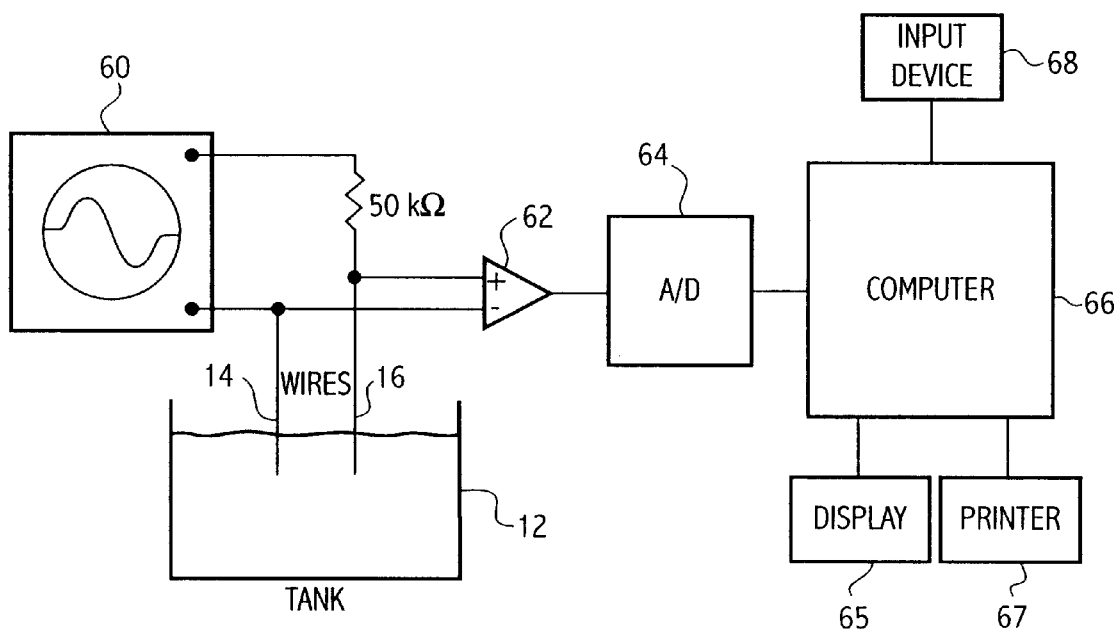
FIG. 2 is a block diagram illustrating the system of the present invention.
Figure 4A:
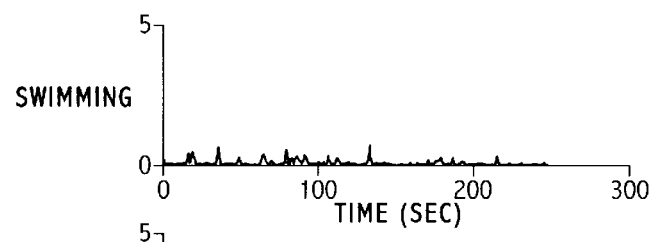
FIGS. 4A–4D are graphical representations of the data representing the behavior of four different animals over time.
Figure 4B:
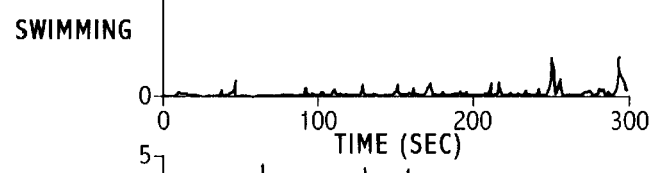
Figure 4C:
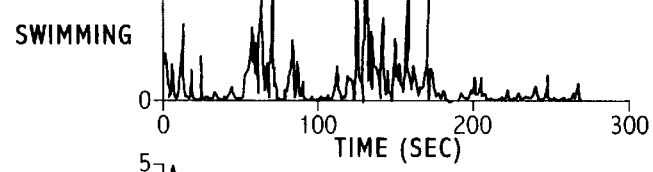
Figure 4D:
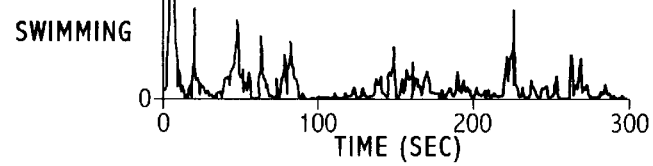
Figure 5A:
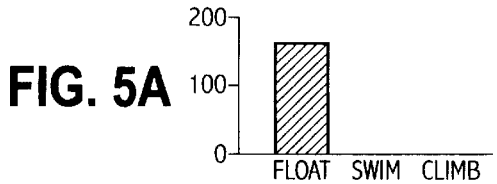
FIGS. 5A–5D are graphical representations respectively corresponding to the animal tests depicted in FIGS. 4A–4D, and illustrating the relative amounts of time that the respective animal was floating, swimming and climbing during the test.
Figure 5B:
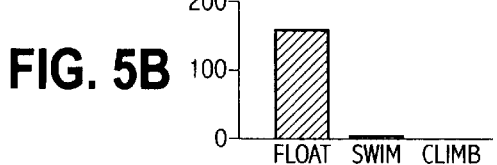
Figure 5C:
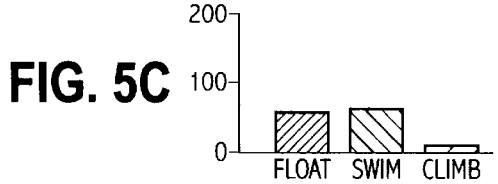
Figure 5D:
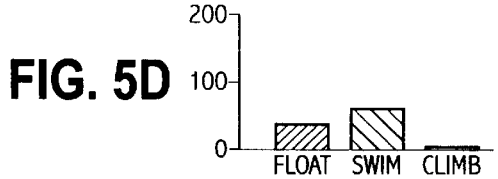

As shown in FIG. 2, a signal generator 60 is coupled to the electrode wires 14 and 16 so as to apply a 200 Hz, 10V amplitude (20V peak-to-peak) sine wave signal to the wires in series with a 50 kΩ resistor. Since the resistance between the wires 14 and 16 is generally on the order of 1 kΩ, the 10V signal in combination with the 50 kΩ resistor acts to a first approximation like a current source, supplying a 200 μA alternating current to the wires. Alternating current is used to avoid electrolysis at the electrodes, which would otherwise rapidly tarnish the wires and cause the appearance of oxygen and hydrogen gas bubbles on the surface of the wires. The voltage across the electrode wires 14 and 16 is picked up by an amplifier 62 and coupled to an analog to digital converter 64. The analog to digital converter 64 digitizes the electrode signal at a rate that is sufficiently high to detect the peaks in the signal. The digital data output from the analog to digital converter 64 is then coupled to a computer 66 that may be a general purpose computer or the like having an input device 68 such as a keyboard and/or mouse.

As discussed in detail below, the computer 66 processes the digitized electrode data in accordance with software that detects the peak values in each cycle of the received sine wave voltage and calculates the root-mean-square (RMS) of the peaks every two seconds. This data is stored as a measure of the energy of the perturbations in the water caused by the animal's movements and an indication of the animal's behavior, i.e. floating, swimming or climbing during that two second period. If there is no activity, the surface of the water remains flat and the conductance between the electrode wires 14 and 16 does not vary so that the amplitude of the sinusoidal voltage is constant and the root-mean-square is zero. However, when the animal swims, the perturbations in the water cause the water height at the electrodes 14 and 16 to vary from moment to moment. As the water height varies, so does the peak of the sinusoidal voltage picked up from the electrodes 14 and 16 so as to produce a non-zero root-mean-square value. The computer 66 stores a plurality of root-mean-square values calculated over the period of the test and generates a graph of these values over time and in real time on the display 65 and/or printer 67.

It is noted, that four behavioral tests can be conducted simultaneously with the present invention by coupling four electrode assemblies to the computer 66, each electrode assembly being positioned in a respective tank of water for testing four different animals. FIGS. 4A, 4B, 4C and 4D illustrate graphical representations of the behavior of four different animals so as to provide an indication of the animals' behavior over time during the test.

The computer 66 processes the electrode signal in accordance with the software depicted by the flow chart of FIG. 3. The computer 66 at a block 70 initiates a continuous 4 kHz digital to analog conversion so as to apply the 10V sine wave to the electrodes 14 and 16. Thereafter, at block 72, the computer 66 initiates a continuous 4 kHz analog to digital conversion of the electrode signal. The computer 66 reads 8000 points of data collected over a two second interval from the analog to digital converter 64 at block 74. This data contains the 200 Hz sine wave amplitude modulated by the movement of the animal in the water of the tank 12. Thereafter, at block 76, the computer 66 searches for 400 peaks that satisfy the criteria of being greater than 0.01 sec. wide and greater than 0.2V. At block 78, the computer 66 determines whether any peaks meet this criteria and if so the computer 66 proceeds to block 80. If no peaks meeting this criteria are detected, the computer proceeds from block 78 to block 82 to provide a warning on the display 65 indicating to the user that the data interface is not functioning properly. At block 80, the computer 66 determines whether any peaks are greater than 4V. If so, the computer 66 proceeds to block 84 to display a warning to the user indicating that the electrodes 14 and 16 are not in proper contact with the tank water or are not connected to the computer interface. If none of the detected peaks are greater than 4V, the computer proceeds directly from block 80 to block 86. At block 86, the computer derives the power spectrum of the 400 collected peaks via a fast fourier transform (FFT). At block 88, the computer filters the electrode signal by excluding frequencies less than 3 Hz and greater than 25 Hz. The lower frequencies of the signal that are filtered are representative of water moving back and forth at the resonant frequency of the tank. This water movement will continue for a while after movement of the animal has stopped. Therefore, it is important to filter out frequencies representative of the movement of the water in the absence of animal movement so as to provide data indicative only of the animal's movement. The computer 66 at block 88 sums the components of the power spectrum between 3 Hz and 25 Hz so as to provide data representative of the root-mean-square of the filtered electrode signal. The root-mean-square value is then divided at block 90 by the result of the average of all of the peak values of the signal so as to normalize the data with respect to the conductance or resistance of the water when at rest. The normalization of the root-mean-square value compensates for variations in the mineral content of the water that is used in the test. Thereafter, the computer 66 at block 92 stores the normalized data point so as to provide a record thereof and also displays the data. One type of graphical representation provided by the system of the present invention is a graph of the normalized root-mean-square values with respect to time. As discussed above, the values calculated and displayed represent the amount of energy of the water perturbations caused by the animals movement in the tank as detected by the electrode assembly 10. The greater the intensity of the swimming activity, the greater the signal.

In order to automatically distinguish between various types of behavior of the animal for example, floating, swimming and climbing, the computer 66 at block 92 compares the value calculated at block 90 to a first threshold used to distinguish between floating and swimming and the computer 66 compares the calculated value to a second threshold that distinguishes between swimming and climbing. If the calculated value is less than the first threshold, which may be on the order of 0.5, the data is interpreted as representing the animal floating. If the calculated value is between 0.5 and 2, the data is interpreted as the animal swimming, and if the calculated value is greater than 2, the data is interpreted as the animal climbing. The computer 66 then generates a bar chart to indicate the relative amounts of time that the animal was floating, swimming and climbing during the test. An example of the bar charts for four different animals, the data for which is graphed over time in FIGS. 4A–4D, is depicted in FIGS. 5A–5D. The data collected for the two animals depicted in FIGS. 4A, 5A and 4B, 5B belong to a different genetic strain than the animals generating the data depicted in FIGS. 4C, 5C and FIGS. 4D, 5D. These two strains of animals show clear differences in the time spent in the three behaviors, floating, swimming and climbing. The difference between the two strains of animals is less evident and difficult to discern when the test is scored by human observation.

It is noted that the teachings of the present invention are not limited to the Porsolt Forced Swim test, this test being only one of a number of behavioral tests indicative of the animal's mental or emotional state which can be measured, evaluated and/or scored in accordance with the teachings of the present invention. Further, there are a number of different methods for detecting swimming or climbing activity in small animals and to generate signals representative thereof, which signals can be processed as described above. For example, in an alternative embodiment of the sensor, ultrasound pulses are directed at the surface of the water and the time it takes for the echo of the pulses to return is measured. As the surface of the water rises and falls, the echo time varies. An ultrasound emitter and detector can be placed directly above the water tank or in the tank near the bottom. In another embodiment, the bulk flow of the water within the tank can be measured wherein the flow of water results from the paddling motion of the animal's feet. In this embodiment, an ultrasound beam is directed at the liquid through the side of the tank, and the Doppler shift of the returned echo is measured. The presence of flow in the water shifts the frequency of the returned echo in proportion to the velocity of the flow. Any motion in the water, in any direction, would indicate that the animal is swimming. In still another embodiment, a thermistor may be placed at the bottom of the tank. A constant current may be applied to the thermistor to heat it to a temperature above the temperature of the surrounding water. The surrounding water will cool the thermistor, but the thermistor will cool more when the water is flowing than when the water is at rest. The voltage across the resistor reflects the amount of flow in the water so as to provide a measure of the animnal's movement or behavior in the water.

In a further embodiment, small metal electrodes may be placed at opposite sides of the tank to detect the electromyograph (EMG) that is generated by the animal's muscles and conducted through the water from the animal. When the animal swims, each leg generates a short (approximately 100 ms) burst of electrical pulses in the frequency range near 100 Hz. The signals are 10 to 50 microvolts in size. The presence of these bursts in the recorded signals can be used to gauge swimming, climbing and head shaking behaviors, each of which has a characteristic frequency spectrum and duration.

In still a further embodiment, a microphone can be used to pick up sound vibrations generated as the animal moves in the water. The microphone can be placed just above the surface of the water to pick up sounds conducted through the air, or the microphone can be placed on the side of the tank to pick up sound waves conducted directly through the water.

It should be apparent that many modifications to the system of the present invention can be made. Thus, it is to be understood that, within the scope of the appended claims, the invention may be practiced otherwise than described herein above.

What is claimed is:

1. A method for automatically measuring an animal's response to his environment as indicative of the animal's mental or emotional state comprising:
   positioning a pair of spaced electrodes in a tank of water in which an animal is placed;
   applying a current to the electrodes;
   measuring the voltage across the electrodes to provide a waveform, the amplitude of which varies with the height of the water in the tank to provide an indication of the animal's behavior; and
   processing the voltage to provide data representing the behavior of the animal as indicative of the animal's mental or emotional state.

2. A method for automatically measuring an animal's response to his environment as indicative of the animal's mental or emotional state as recited in claim 1 including the step of displaying a graphical representation of the animal's behavior over time.

3. A method for automatically measuring an animal's response to his environment as indicative of the animal's mental or emotional state as recited in claim 1 including the step of comparing the processed voltage to a threshold to distinguish between water height fluctuations indicative of the animal swimming and indicative of the animal floating.

4. A method for automatically measuring an animal's response to his environment as indicative of the animal's mental or emotional state as recited in claim 1 wherein said electrodes are positioned in the tank in a manner to prevent the animal from using the electrodes to climb out of the tank.

5. A method for automatically measuring an animal's response to his environment as indicative of the animal's mental or emotional state as recited in claim 1 including the step of filtering the waveform to remove lower frequencies associated with water movement in the absence of animal movement.

6. A method for automatically measuring an animal's response to his environment as indicative of the animal's mental or emotional state as recited in claim 1 including the step of applying an alternating current to the electrodes wherein the animal's behavior modulates the amplitude of the measured voltage.

7. A method for automatically measuring an animal's response to his environment as indicative of the animal's mental or emotional state as recited in claim 1 including the step of normalizing the voltage to the conductivity of the water when at rest.

8. A method for automatically measuring an animal's response to his environment as indicative of the animal's mental or emotional state as recited in claim 1 determining the peak values of the measured waveform over an interval; processing the peak values determined over the interval to provide a behavior indicative value used to generate the graphical representation of the animal's behavior.

9. A method for automatically measuring an animal's response to his environment as indicative of the animal's mental or emotional state comprising:

positioning a sensor in an environment of a tank of water in which an animal is placed to measure an attribute of the environment that varies with the animal's behavior and to generate a signal representative of the measured attribute and animal's behavior wherein said measured attribute is the energy of water perturbations caused by the animal's movement;

filtering the signal to remove lower frequencies associated with water movement in than absence of animal movement; and processing the signal to provide a graphical representation of the animal's behavior indicative of its mental or emotional state.

10. A method for automatically measuring an animal's response to his environment as indicative of the animal's mental or emotional state comprising:

positioning a sensor in an environment of a tank of water in which an animal is placed to measure an attribute of the environment that varies with the animal's behavior and to generate a signal representative of the measured attribute and animal's behavior wherein said measured attribute is the fluctuation in the height of the water;

filtering the signal to remove lower frequencies associated with water movement in the absence of animal movement; and processing the signal to provide a graphical representation of the animal's behavior indicative of its mental or emotional state.

11. A method for automatically measuring an animal's response to his environment as indicative of the animal's mental or emotional state comprising:

positioning a sensor in an environment of a tank of water in which an animal is placed to measure an attribute of the environment that varies with the animal's behavior and to generate a signal representative of the measured attribute and animal's behavior wherein said measured attribute is sound generated by the animal's movement in the water;

filtering the signal to remove lower frequencies associated with water movement in the absence of animal movement; and processing the signal to provide a graphical representation of the animal's behavior indicative of its mental or emotional state.

12. A method for automatically measuring an animal's response to his environment as indicative of the animal's mental or emotional state comprising:

positioning a sensor in an environment of a tank of water in which an animal is placed to measure an attribute of the environment that varies with the animal's behavior and to generate a signal representative of the measured attribute and animal's behavior wherein said measured attribute is the flow of water through the tank generated by the animal's movement;

filtering the signal to remove lower frequencies associated with water movement in the absence of animal movement; and processing the signal to provide a graphical representation of the animal's behavior indicative of its mental or emotional state.

13. A method for automatically measuring an animal's response to his environment as indicative of the animal's mental or emotional state comprising:

sensing an attribute of the animal's environment that varies with the animal's behavior in that environment to generate a waveform, the amplitude of which is modulated by the animal's behavior in the environment;

filtering the waveform to remove frequencies not associated with the animal's behavior;

determining peak values of the waveform satisfying predetermined criteria;

processing the peak values to provide a graphical representation of the behavior of the animal indicative of the animal's mental or emotional state; and comparing the processed peak values to a plurality of thresholds, each threshold defining a change in the animal's behavior from one type of behavior to another type of behavior and providing a graphical representation of the relative amounts of each type of behavior.

14. A method for automatically measuring an animal's response to his environment as indicative of the animal's mental or emotional state comprising:

sensing an attribute of the animal's environment that varies with the animal's behavior in that environment to generate a waveform, the amplitude of which is modulated by the animal's behavior in the environment, wherein said sensing step includes the steps of positioning a pair of spaced electrodes in a tank of water in which an animal is placed;

applying a current to the electrodes; and measuring the voltage across the electrodes to provide the waveform, the amplitude of which is modulated by the animal's movement in the water; filtering the waveform to remove frequencies not associated with the animal's behavior; determining peak values of the waveform satisfying predetermined criteria; and processing the peak values to provide a graphical representation of the behavior of the animal indicative of the animal's mental or emotional state.

15. A method for automatically measuring an animal's response to his environment as indicative of the animal's mental or emotional state as recited in claim 14 including the steps of comparing the processed values to at least one threshold to distinguish between voltage amplitudes which are indicative of the animal swimming and indicative of the animal floating.

16. A method for automatically measuring an animal's response to his environment as indicative of the animal's mental or emotional state as recited in claim 15 including providing a graphical representation illustrating the relative amounts of time that the animal was swimming and floating.

17. A system for measuring an animal's response to his environment indicative of the animal's mental or emotional state comprising:

a pair of spaced electrodes for at least partial immersion in a tank of water in which an animal is placed to provide a signal that varies with movement of the animal in the water;

a signal generator coupled to the electrodes to apply a current thereto; and a filter to remove low frequency components of the electrode signal associated with movement of the water in the absence of animal movement to provide data indicative of the animals mental or emotional state.

18. A system for measuring an animal's response to his environment indicative of the animal's mental or emotional state as recited in claim 17 further including an analog to digital converter for converting the signal provided by the electrodes to digital data; and software for processing the digital data to provide a graphical representation of the behavior of the animal indicative of the animal's mental or emotional state.

19. A system for measuring an animal's response to his environment indicative of the animal's mental or emotional state as recited in claim 18 wherein said filter is a software filter.

20. A system for measuring an animal's response to his environment indicative of the animal's mental or emotional state as recited in claim 18 including software to determine over each of a plurality of intervals the root mean square of the filtered signal to provide data used to generate the graphical representation of the animal's behavior.

21. A system for measuring an animal's response to his environment indicative of the animal's mental or emotional state as recited in claim 18 including software for normalizing the data with respect to a value representing the resting conductivity of the water.

22. A system for measuring an animal's response to his environment indicative of the animal's mental or emotional state as recited in claim 21 including software to generate a graph of the normalized data over time.

23. A system for measuring an animal's response to his environment indicative of the animal's mental or emotional state as recited in claim 22 including software to generate a graphical representation illustrating the relative amounts of time that the animal was swimming and floating during a test.

24. A system for measuring an animal's response to his environment indicative of the animal's mental or emotional state as recited in claim 18 including software for comparing the processed data to a threshold value to distinguish between water heights indicative of the animal swimming and indicative of the animal floating.

25. A system for measuring an animal's response to his environment indicative of the animal's mental or emotional state as recited in claim 17 wherein the electrodes are mounted on a plate having a clip thereon for attaching the plate to the tank, the plate having a generally smooth surface and rounded edges.

26. A system for measuring an animal's response to his environment indicative of the animal's mental or emotional state as recited in claim 17 wherein the electrodes are disposed in spaced channels formed in a wall of the tank.

* * * * *